(12) United States Patent
Niklaus

(10) Patent No.: US 10,912,886 B2
(45) Date of Patent: Feb. 9, 2021

(54) VALVE CLUTCH DEVICE AND DOSING UNIT WITH A VALVE CLUTCH DEVICE

(71) Applicant: Roche Diabetes Care, Inc., Indianapolis, IN (US)

(72) Inventor: Hanspeter Niklaus, Riken (CH)

(73) Assignee: Roche Diabetes Care, Inc., Indianapolis, IN (US)

(*) Notice: Subject to any disclaimer, the term of this patent is extended or adjusted under 35 U.S.C. 154(b) by 186 days.

(21) Appl. No.: 15/908,411

(22) Filed: Feb. 28, 2018

(65) Prior Publication Data

US 2018/0185573 A1 Jul. 5, 2018

Related U.S. Application Data

(63) Continuation of application No. PCT/EP2016/070202, filed on Aug. 26, 2016.

(30) Foreign Application Priority Data

Sep. 3, 2015 (EP) ..................................... 15183669

(51) Int. Cl.
*A61M 5/168* (2006.01)
*A61M 5/142* (2006.01)
(Continued)

(52) U.S. Cl.
CPC .... *A61M 5/16809* (2013.01); *A61M 5/14216* (2013.01); *A61M 39/223* (2013.01);
(Continued)

(58) Field of Classification Search
CPC .......... A61M 5/14216; A61M 5/16809; A61M 2205/3337; A61M 2205/3396;
(Continued)

(56) References Cited

U.S. PATENT DOCUMENTS

2013/0261599 A1* 10/2013 Haueter ............ A61M 5/14216
604/506

FOREIGN PATENT DOCUMENTS

EP 1970677 A1 9/2008
EP 2163273 A1 3/2010
(Continued)

OTHER PUBLICATIONS

International Search Report and Written Opinion of the International Searching Authority; PCT/EP2016/070202; dated Nov. 11, 2016; 9 pages.

*Primary Examiner* — Nathan R Price
*Assistant Examiner* — Tania Ismail
(74) *Attorney, Agent, or Firm* — Bose McKinney & Evans LLP

(57) ABSTRACT

A valve clutch that has a central member extending along a central axis and includes a drive coupler that receives a driving torque. A coupling member is provided that includes coupling pins extending parallel to the central axis. A valve is rotatably disposed around the central axis between inlet and outlet positions. A sleeve is configured to rotationally engage the valve, the sleeve including at least one clamping member. The valve clutch is reversibly changeable between (1) an unengaged configuration wherein a driving torque received by the central member is not transmitted to the sleeve member, and (2) an engaged configuration wherein the at least one coupling pin is clamped between the central member and the at least one clamping member, thereby transmitting the driving torque that is received by the central member via the sleeve member to the valve member.

14 Claims, 6 Drawing Sheets

(51) Int. Cl.
*A61M 39/22* (2006.01)
*F16K 31/04* (2006.01)

(52) U.S. Cl.
CPC ..... *A61M 39/22* (2013.01); *A61M 2205/3337* (2013.01); *A61M 2205/3396* (2013.01); *F16K 31/043* (2013.01)

(58) Field of Classification Search
CPC ... A61M 39/233; A61M 39/22; F16K 31/043; F16K 251/77
See application file for complete search history.

(56) References Cited

FOREIGN PATENT DOCUMENTS

| | | | |
|---|---|---|---|
| EP | 2295096 A1 | 3/2011 | |
| EP | 2361646 A1 | 8/2011 | |
| EP | 2457602 A1 | 5/2012 | |
| EP | 2510960 A1 | 10/2012 | |
| EP | 2510961 A1 | 10/2012 | |
| EP | 2510962 A1 | 10/2012 | |
| EP | 2753380 | 7/2014 | |
| EP | 2696915 B1 | 5/2017 | |
| WO | WO 2012/069308 A1 | 5/2012 | |
| WO | WO 2013/029999 A1 | 3/2013 | |
| WO | WO 2013/034159 A1 | 3/2013 | |
| WO | WO-2013034159 A1 * | 3/2013 | ........ A61M 5/14216 |

* cited by examiner

VALVE CLUTCH DEVICE AND DOSING UNIT WITH A VALVE CLUTCH DEVICE

RELATED APPLICATIONS

This application is a continuation of PCT/EP2016/070202, filed Aug. 26, 2016, which claims priority to EP 15183669.9, filed Sep. 3, 2015, the entire disclosures of both of which are hereby incorporated by reference.

The present disclosure lies in the field of dosing units for liquid drugs as used in the context of drug infusion. This disclosure further lies in the field of valve clutch devices that form part of some dosing units.

Ambulatory infusion devices are well known in the art for the administration of liquid drugs, for example in the therapy of Diabetes Mellitus by Continuous Subcutaneous Insulin Infusion (CSII) as well as in pain therapy or cancer therapy. Ambulatory infusion devices are available from a number of supplies, such as Roche Diagnostics GmbH, Germany, or Medtronic MiniMed Inc., CA, USA.

EP 1970677 A1 discloses a system with a miniaturized metering piston pump with a dosing cylinder that is repeatedly coupled to and filled from a larger reservoir, followed by coupling the dosing cylinder to an infusion site and infusing the liquid drug out of the dosing cylinder in incremental steps and over an extended time period via displacing a piston. For alternatively coupling the dosing cylinder to the reservoir and the infusion site, a valve system is proposed. Reference is made to EP 1970677 A1 for the basic operational principle and design of a dosing unit in accordance with the present document.

Generally, a miniaturized metering piston pump according to the principle as laid down in EP 1970677 A1 is in this document referred to as "dosing unit." More particularly, the dosing unit is a generally disposable fluidic unit that is, for its application, coupled to further infusion pump components or devices, such as a drive unit which may include one or more actuators/motors, an electronic control unit, a liquid drug reservoir, and an infusion cannula, and is discarded after a use period of generally a few days up to two weeks.

Particular aspects and embodiments of dosing units and their operation that may be applied, alone or in combination, in the context of this disclosure are disclosed in e.g., EP 2510962, EP 2510960, EP 2696915, EP 2457602, WO 2012/069308, WO 2013/029999, EP 2753380, EP 2163273, and EP 2361646.

SUMMARY

Dosing units of the before-mentioned type may, in some embodiments, be realized with a single actuator (typically a motor) that is used for both valve switching and piston displacement. For those embodiments, however, the coupling mechanism for selectively coupling the drive with the valve and/or the piston is a particularly critical aspect. Favorably, valve switching shall be possible at any piston position within the cylinder by simply reversing the driving direction. Furthermore, the process of valve switching shall be associated with no or substantially no piston displacement in order to minimize dosing errors.

Further requirements that are to be met as far as possible are high reliability over the usage time, small dimensions and cost-efficiency since the coupling mechanism is part of a generally disposable product.

This disclosure improves the state of the art in the field of liquid drug dosing units. Favorably, some or all of the disadvantages of prior art solutions can be avoided or reduced.

In an aspect, this disclosure provides a valve clutch device. The valve clutch device includes a central member. The central member extends along a central axis and includes a drive coupler that is designed to receive a driving torque around the central axis.

The valve clutch device further includes a coupling member. The coupling member includes at least one coupling pin extending parallel to the central axis.

The valve clutch device further includes a valve member. The valve member is beared rotatable around the central axis between an inlet valve position and an outlet valve position.

The valve clutch device further includes a sleeve member. The sleeve member is designed to rotationally engage the valve member and includes at least one clamping member.

The valve clutch device is reversibly changeable between an unengaged configuration where a driving torque that is received by the central member is not transmitted to the sleeve member and an engaged configuration where the at least one coupling pin is clamped between the elongated central member and the at least one clamping member, thereby transmitting a driving torque that is received by the central member via the sleeve member to the valve member.

In some embodiments of the valve clutch device, the at least one coupling pin is in frictional engagement with the central member.

In some embodiments of the valve clutch device, the frictional engagement of the at least one coupling pin and the central member is changeable between a sliding frictional engagement and a sticking frictional engagement in dependence of an angular position of the at least one coupling pin relative to the central member and/or in dependence of a direction of rotation of the central member around the central axis. The sticking frictional engagement may also be a clamping engagement where the at least one coupling pin is clamped between the central member and the clamping member and is accordingly in sticking frictional engagement with the central member as well as with the clamping member.

In some embodiments of the valve clutch device, the valve clutch device includes angularly spaced coupling pin blocks and a clamping member is arranged angularly symmetrical between two adjacent coupling pin blocks.

In some embodiments of the valve clutch device, the coupling pin blocks are formed by arm members of the valve member, the arm members extending generally parallel to the central axis.

The arm members of such embodiments project, in an assembled state, in distal direction from a valve member body, with gaps being present between the arm members.

In some embodiments of the valve clutch device, the coupling member includes a plurality of coupling pins and the sleeve member includes a corresponding plurality of associated clamping members. In an exemplary embodiment, three coupling pins and three associated clamping members are present, but another number of clamping members and coupling pins may be used as well. Generally, the coupling pins and clamping members are angularly symmetrically distributed.

In some embodiments of the valve clutch device, the central member includes a threaded central member section with an outer thread and the valve member includes a corresponding inner thread. By applying a drive torque to the central member, the central member can move in a screw-like manner relative to the valve member.

In some embodiments, the valve clutch device includes a valve member block, the valve member block blocking rotational movement of the valve member in the inlet valve position and the outlet valve position, respectively. In an embodiment, the valve member block is realized by a rim that extends along the valve member parallel to the central axis and is arranged to selectively abut and thereby engage blocking edges of a stationary member of a dosing unit or other blocking elements as generally known in the art, such as blocking pins, blocking protrusions or the like.

In some embodiments of the valve clutch device, the coupling member includes a coupling member base, the coupling member base being rotatably arranged around the central member with the at least one coupling pin projecting from the coupling member base. The coupling member base may especially be disc shaped and have an, e.g., circular aperture in which, in an assembled state, the central member is received.

In some embodiments of the valve clutch device, the central member, the coupling member, the sleeve member and the valve member are arranged coaxially with the central axis.

In some embodiments of the valve clutch device, the central member is arranged in sealing and sliding engagement inside the valve member, the central member thereby serving as piston member.

In some embodiments of the valve clutch device, the drive coupler is designed for receiving a drive pin in sliding engagement along the central axis and in substantially rigid rotational engagement with respect to the central axis. Other types of drive engagement, such as a toothed engagement, may be used as well.

In some embodiments of the valve clutch device, the valve member includes a cylinder and a valve member aperture in fluid communication with an inner volume of the cylinder.

In a further aspect, this disclosure provides a liquid drug dosing unit. The liquid drug dosing unit includes a valve clutch device as discussed before. The liquid drug dosing unit further includes a stationary member. The stationary member bears the valve member sealing and rotatable around the central axis. The stationary member further includes an inlet aperture and an outlet aperture, wherein the valve member aperture is in fluidic communication with the inlet aperture in the inlet valve position and alternatively in fluidic communication with the outlet aperture in the outlet vale position.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
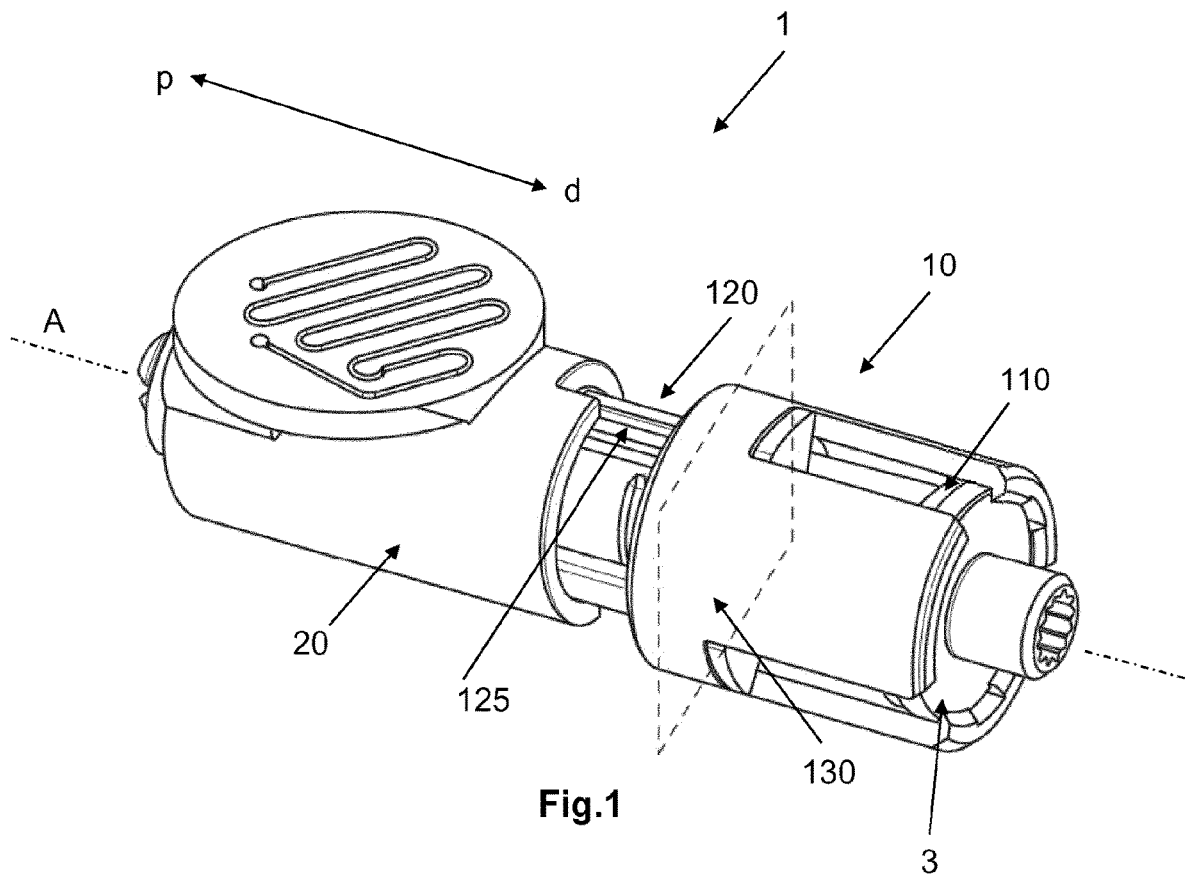
FIG. 1 shows a dosing unit in accordance with the present disclosure in a perspective view.
Figure 2:
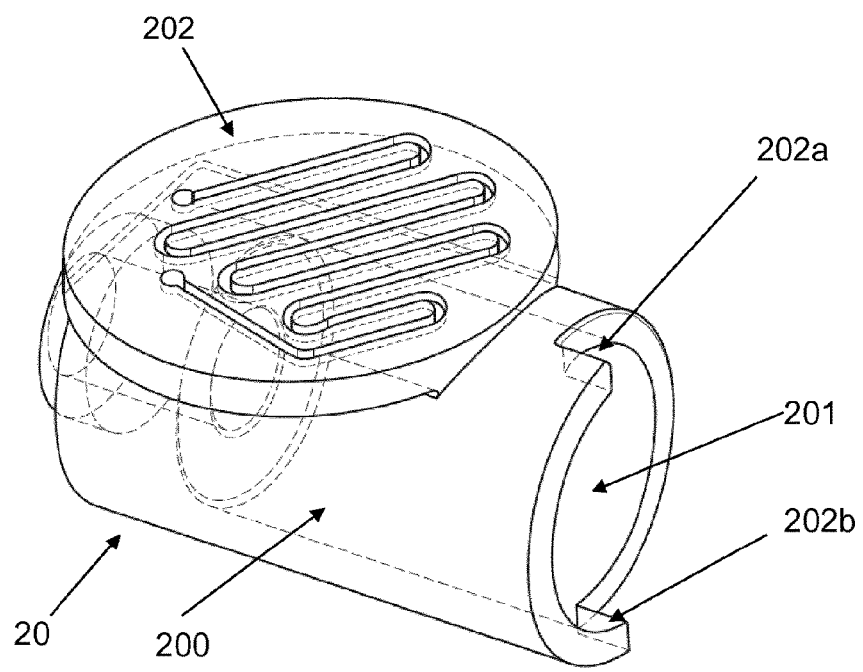
FIG. 2 shows a stationary member in an isolated perspective view.

In the following, reference is first made to FIG. 1 and FIG. 2. FIG. 1 shows a dosing unit 1 in accordance with the present disclosure in a perspective view. The dosing unit 1 includes a valve clutch device 10 in accordance with the present disclosure and a stationary member 20. The stationary member is shown in FIG. 2 in an isolated perspective view.

In this document, the directional terms "proximal" and "distal" are used as follows: A movement of the piston of the dosing unit along the central axis that decreases the liquid filled volume of the dosing unit is a movement from the distal into the proximal direction. Likewise, a movement of the piston that increases the liquid-filled volume is a movement from the proximal into the distal direction. A piston movement into the proximal direction is also referred to as "advancement," while a piston movement into the distal direction is also referred to as "retraction." In FIG. 1, the proximal and distal directions are indicated by "p" and "d," respectively. In the further figures that show individual components of the dosing unit 1, the same perspective is used.

With respect to the figures, it is further noted that features that are present more than once in the same or substantially the same way are generally only referenced once. Furthermore, features that are visible in more than one figure may not be referenced in all of them.

The stationary member 20 has a stationary member body 200 and a stationary member recess 201. The stationary member recess 201 has a generally cylindrical inner contour and bears, in an assembled state, a valve member 120 sealing and rotatable around a central axis A. The stationary member 200 has two blocking edges 202a, 202b and the valve member 120 has a longitudinal rim 125 that selectively engages the blocking edges 202a, 202b. As will be explained further below, the rim 125 further serves for coupling the valve member 120 with the sleeve member 130.

In combination, the blocking edges 202a, 202b and the rim 125 form a valve member block that limits the rotational movement of the valve member 120 to a range between an inlet valve position and an outlet valve position of 180° in exemplary embodiments.

At its proximal end, the valve member 120 comprises valve member aperture (not visible). In the inlet valve position, the valve member aperture is aligned and thereby in communication with the inlet aperture (not visible) of the stationary member 200. In the outlet valve position, the valve member aperture is aligned and thereby in communication with the outlet aperture (not visible) of the stationary member 200. In the rotational position between the inlet valve position and the outlet valve position, the valve member aperture is generally fluidically isolated from both the inlet aperture and the outlet aperture.

In an operational state, the fluidic inlet aperture is fluidically coupled with the drug reservoir, such as an insulin reservoir, while the outlet aperture is fluidically coupled with an infusion cannula either directly or via an infusion line, such as a tubing.

The stationary member 20 further includes an optional fluidic platform 202. The fluidic platform 202 comprises a fluidic pressure sensor coupled with the outlet aperture and arranged between the outlet aperture and the infusion cannula. Further disclosure regarding this type of pressure sensor can be found in the EP 2295096. This type of pressure sensor, however, is not essential. Other types of pressure sensors as well as further sensors such as flow sensors, may be used additionally, or alternatively. In further embodiments, no sensors are present.

Inside the valve member 120, a central member 100 (shown in FIG. 4) is coaxially arranged in threaded engagement as will be explained further below. A sleeve member 130 is coaxially arranged around the valve member 120.

Figure 3:
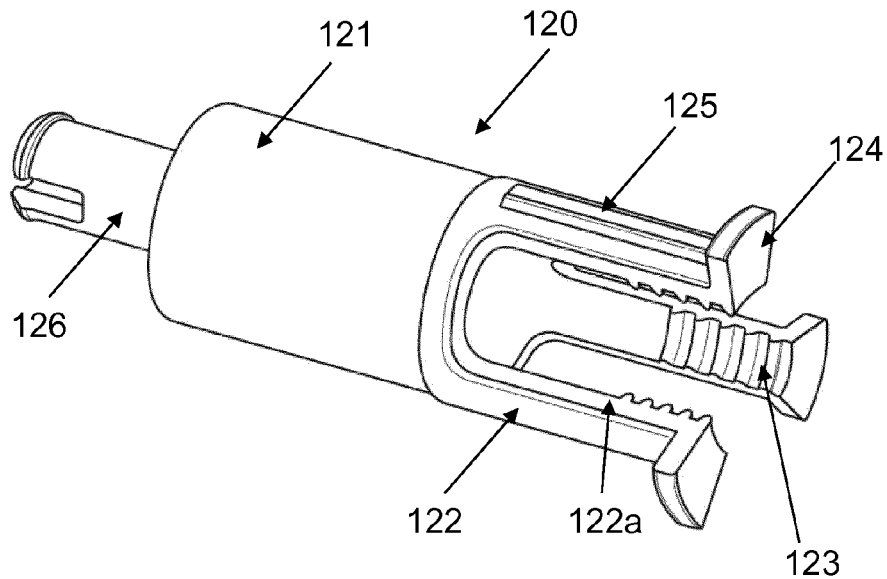
FIG. 3 shows a valve member in an isolated perspective view.
Figure 4:
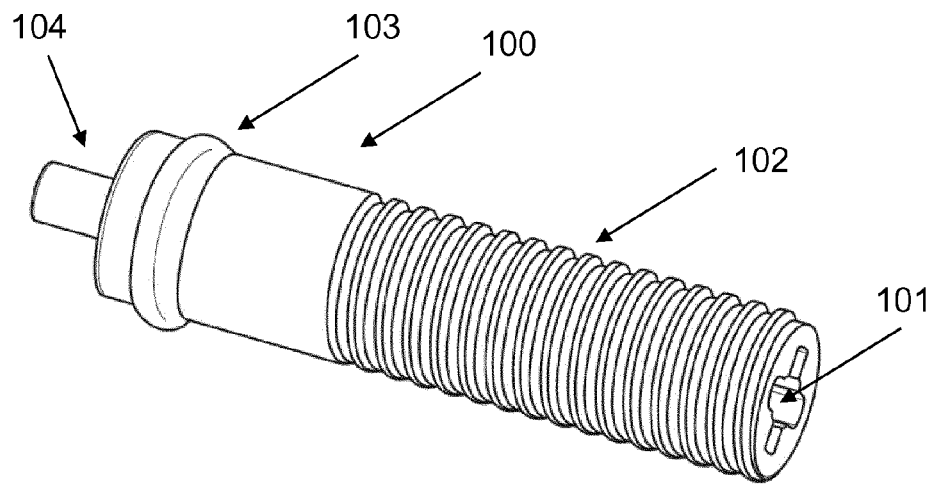
FIG. 4 shows a central member in an isolated perspective view.

In the following, reference is additionally made to FIG. 3, and FIG. 4. showing the valve member 120 and the central member 100 in an isolated perspective views, respectively. FIG. 3 shows the valve member 120 in an isolated view and FIG. 4 shows the central member 100 in an isolated view. The valve member 120 has a generally elongated shape with a hollow cylindrical valve member body 121 that is sealing and rotational received by the stationary member access 201 as explained before. In distal direction, exemplarily three arm members 122 project from the valve member body 121.

In a rear or distal end section, the three arm members 122 have an inner thread 123. The inner thread 123 is designed for favorably free play engagement with a corresponding outer thread 102 of the central member 100. Favorably, the arm members 122 exert some inwards-directed radial force, thus biasing the threaded engagement.

At their rear or distal ends, the arm members 122 have radially outwards-directed protrusions 124. The function of the protrusions 124 will be discussed further below in the context of the valve operation. The circumferential surfaces of the arm members 122 further serve as coupling pin blocks 122a as will also be discussed in the context of valve operation.

In a front or proximal end section, the valve member 120 has a generally cylindrical valve member head 126, that is designed for engaging the stationary member 200 in exemplary embodiments via a biased snap fit (see also FIG. 1).

The central member 100 has an elongated body (not referenced) that carries, in a rear or distal section, the before-mentioned outer thread 102. Proximal from the outer thread 102, the central member 100 has a protruding circumferential central member seal 103 that is designed to be sealing and sliding received by the hollow cylinder of the valve member 120.

Via the engagement of the outer thread 102 with the inner threaded segments 123, the central member 100 is movable relative to the valve member 120 along the central axis A in a screw-like way between a most retracted and a most advanced position. The length of the outer thread 102 corresponds to or is somewhat larger than the displacement range between the most retracted and the most advanced position.

For a given relative position of the central member 100 relative to the valve member 120, a volume exists inside the valve member body 121 that is generally fluidically isolated, but may, via the valve member aperture as explained before, be in fluidic communication with the inlet valve aperture in the inlet valve position or with the outlet valve aperture in the outlet valve position, respectively. The valve member 120 accordingly serves as cylinder and the central member 100 serves as piston. Liquid can be drawn into the cylinder by moving central member/piston 100 in the retracted (distal) direction with the valve member aperture being in fluidic communication with the inlet aperture. Similarly, liquid can be expelled out of the cylinder by moving the central member/piston 100 into the advanced (proximal) direction with the valve member aperture being in fluidic communication with the outlet aperture.

At its proximal end, the central member 100 has a generally cylindrical central member head 104 of reduced outer diameter as compared to the central member body. In the most advanced (most proximal) position of the central member 100 relative to the valve member 120, the central member head 104 is received inside the valve member head 126. It is to be noted, however, that the presence of the valve member head 126 and the central member head 104 is not essential. Alternatively, the proximal front surface of the central member 100 and the inner front surface of the valve member body 121 may be flat or have another suited shape.

In a rear or distal section, generally overlapping with the outer thread 102, the central member 100 further has a drive coupler 101. The drive coupler 101 is exemplarily realized by a an elongated recesses 101 that extends along the central axis A and has a non-circular (exemplarily cross-shaped) cross section.

Figure 5:
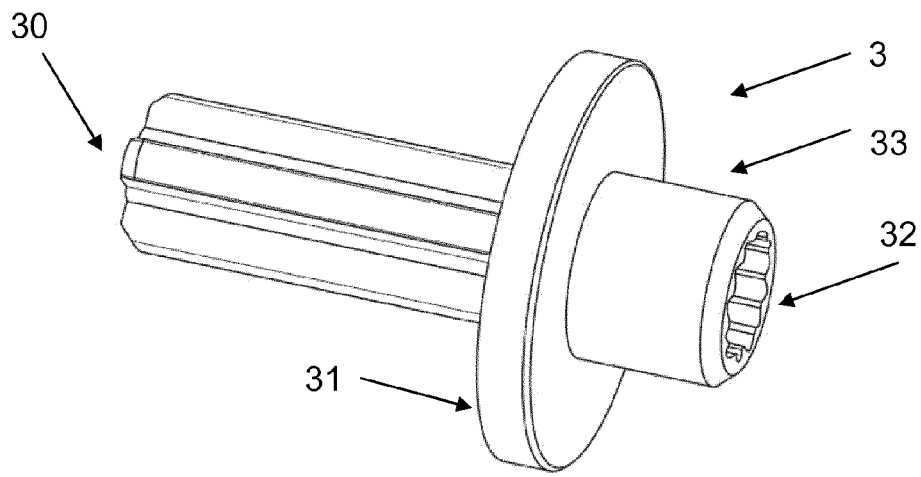
FIG. 5 shows a drive member in an isolated perspective view.

In the following, reference is additionally made to FIG. 5. FIG. 5 shows the drive member 3 in an isolated perspective view. The drive member 3 is of generally elongated shape and comprises an elongated drive pin 30 of non-circular cross section. The drive pin 30 is dimensioned to fit into the recesses 101 with sliding and substantially free play engagement. At its distal end, the drive member 3 comprises an motor coupler 32 that is exemplarily realized as non-circular recesses of, for example, star-shaped cross-section. Via the motor coupler 32, the drive member 3 receives, in operation, a drive torque that is transmitted to the central member 100 and/or the valve member 120 as will be explained further below. The motor coupler 32 is arranged in a cylindrical distal section 33 of the drive member 3.

Figure 6:
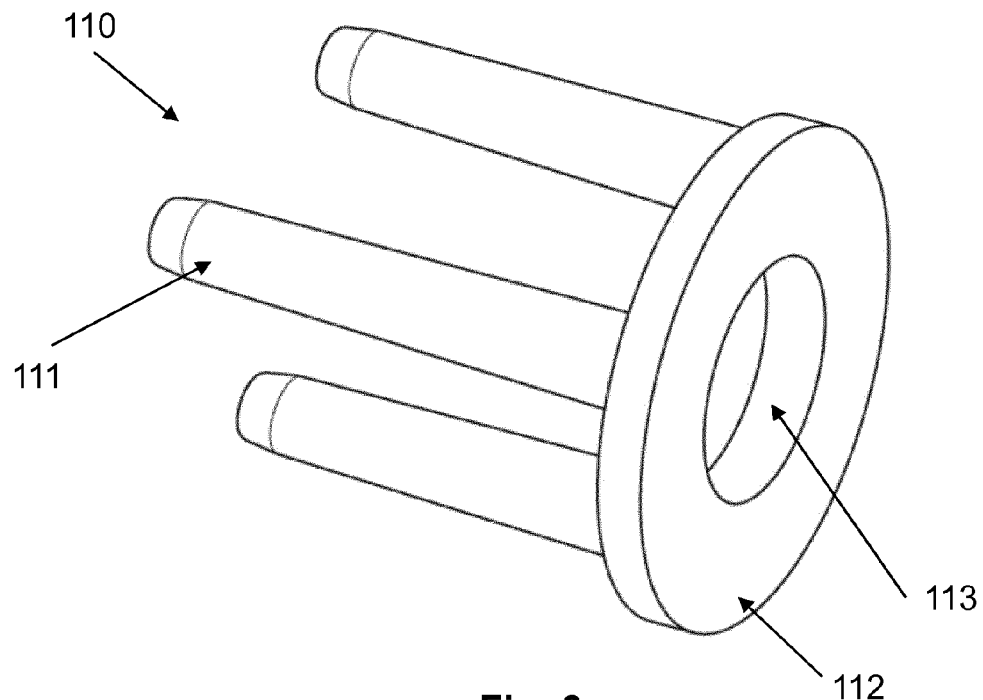
FIG. 6 shows a coupling member in an isolated schematic view.

In the following, reference is additionally made to FIG. 6. FIG. 6 shows the coupling member 110 of the valve clutch device 10 in an isolated perspective view. The coupling member 110 comprises a disk-shaped coupling member base 112 with a central bore-like through-opening 113. The through-opening 113 is dimensioned to receive the distal section 33 of the drive member 3 in sliding engagement, such that the coupling member base 112 is arranged rotatable around the central member drive member 3. In an assembled state, the coupling member 110 is arranged proximal of the drive member 3.

In exemplary embodiments, three coupling pins 111 project from the coupling member base 112 in the proximal direction. In an assembled state, they extend parallel to and around the threaded central member section 102 and contact the threaded central member section 102 in frictional engagement.

Figure 7:
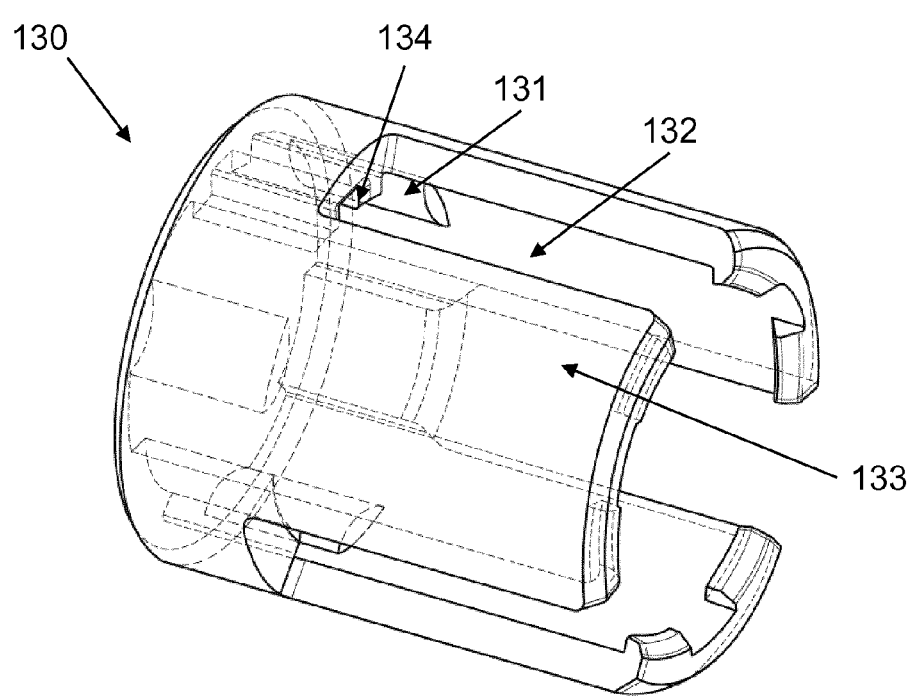
FIG. 7 shows a sleeve member in an isolated schematic view.

In the following, reference is additionally made to FIG. 7. FIG. 7 shows the sleeve member 130 of the of clutch device 10 in an isolated perspective view. The sleeve member 130 has a general tubular shape with a sleeve body 133. The sleeve member 130 comprises longitudinal sleeve slots 132 that correspond in numbers to the arm members 122 of the valve member 120. In an assembled state, the sleeve member 130 is arranged around the coupling member 110 and the central member 100. Further in the assembled state, the protrusions 124 radially project into the sleeve slots 132. The engagement of the protrusions 124 with the sleeve slots rotationally coupled, together with the engagement of the rim 125 with the notch 134, the valve member 120 with the sleeve member 130.

In a proximal section, proximal to the sleeve slots 132, the sleeve member 130 further comprises a notch 134, the notch 134 extending axially on the inside of the coupling sleeve 130. In an assembled state, the notch 134 receives and operationally engages the rim 125 of the valve member 120, thus rotatable coupling the valve member 120 and the sleeve member 130.

The sleeve device 130 further comprises a number of clamping members 131 in form of protrusions that extend radially inward from the body of the sleeve member 130 in a proximal section of the sleeve member 130, as best visible in the following figures. The clamping members 131 have a convex cross section and are designed to selectively clamping the coupling pins 111 to the threaded central member section 102.

In the following, operation of the dosing unit 1 and in particular of the valve clutch device 10 will be described with additional reference to FIG. 8 and FIGS. 9a-9e. As will become more readily apparent in the following, the valve clutch device 10, and in particular the coupling member 110 and the sleeve member 130 are core elements this embodiment of a valve clutch device 10. In a first configuration, providing a drive torque allows the central member 100 to move inside and relative to the valve member 120 in a screw-like manner, with the valve member 120 staying in rest. The corresponding configuration of the valve clutch device 10 is referred to as "unengaged configuration." In the unengaged configuration, liquid can be drawn into the dosing unit 1 by moving the central member 100—which serves as piston—into the distal direction. Similarly, liquid can be expelled out of the dosing unit 1 by moving the central member 100 into the proximal direction.

In the alternative "engaged configuration," the central member 100 and the valve member 120 are rotationally coupled via the coupling member 110 and the sleeve member 130. In the engaged configuration, a drive torque that is applied to the central member 100 is transmitted to the valve member 120. Consequently, the central member 100 and the valve member 120 are rotated relative to and inside the stationary member 20 between the inlet valve position and the outlet valve position, respectively. Between the central member 100 and the valve member 120, no relative movement occurs in the engaged configuration.

Figure 8:
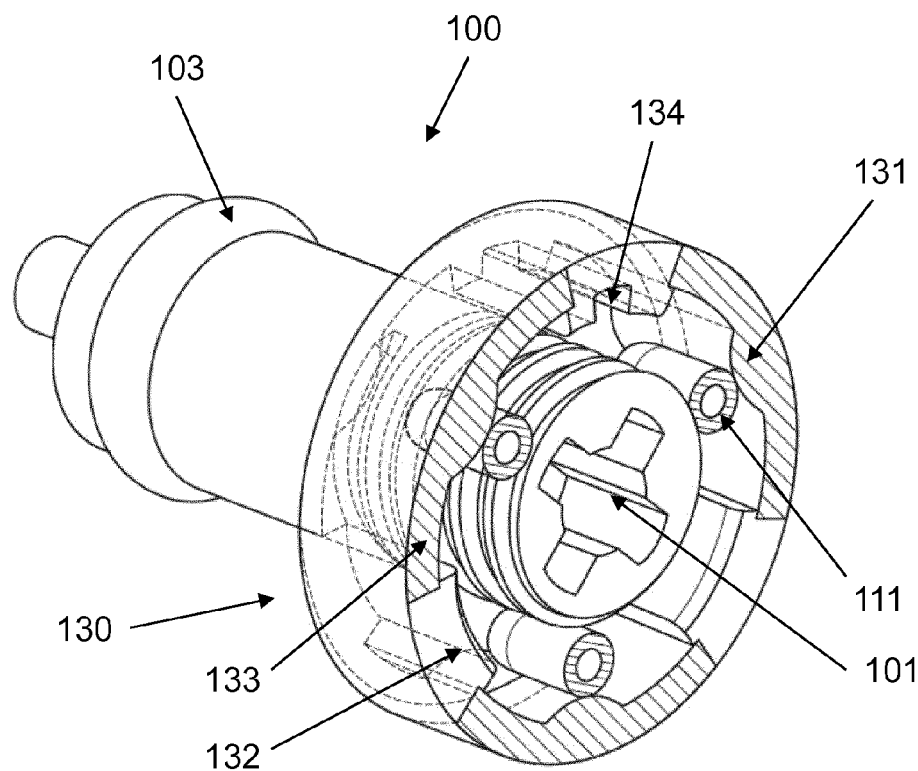
FIG. 8 shows some components of a valve clutch device in an assembled cross-sectional view.

FIG. 8 shows the central member 100, the sleeve member 130, and the coupling pins 111 of the coupling member 110 in a perspective sectional view and in an assembled state, with the section plane being indicated in FIG. 1. FIG. 8 shows the components in the engaged configuration of the valve clutch device 10.

In the engaged state, the clamping members 131 clamp the coupling pins 111 against the central member 100 (more particularly, against the threaded central member section 102), such that sticking friction is present between the central member 100 and the coupling pins 111, as well as between the coupling pins 111 and the sleeve member 130. No relative motion between the central member 100, the coupling member 110, and the sleeve member 130 can accordingly occur in this engaged configuration. Exerting a driving torque onto the central member 100 accordingly results in a common rotational movement of the central member 100, the coupling member 110, and the sleeve member 130 in the engaged configuration. Furthermore, since the valve member 120 is rotationally coupled to the sleeve member 120 via an engagement of the rim 125 and the notch 134, also the valve member 120 moves together with the sleeve member 130 in the engaged configuration.

In the unengaged configuration, the central member 100, the coupling pins 111, and the sleeve member 130 are, in contrast, rotatable relative to each other. In particular, the coupling pins 111 are not clamped by the clamping members 131 and can accordingly not transmit a driving torque from the central member 100 to the sleeve member 130. The central member 100 can accordingly rotate independent from the sleeve member 130 and the valve member 120 in the unengaged configuration.

The sectional drawings of FIGS. 9a to 9e illustrate the operation of the valve clutch device 10 for switching between the inlet valve position and the outlet valve position, respectively.

Figure 9A:
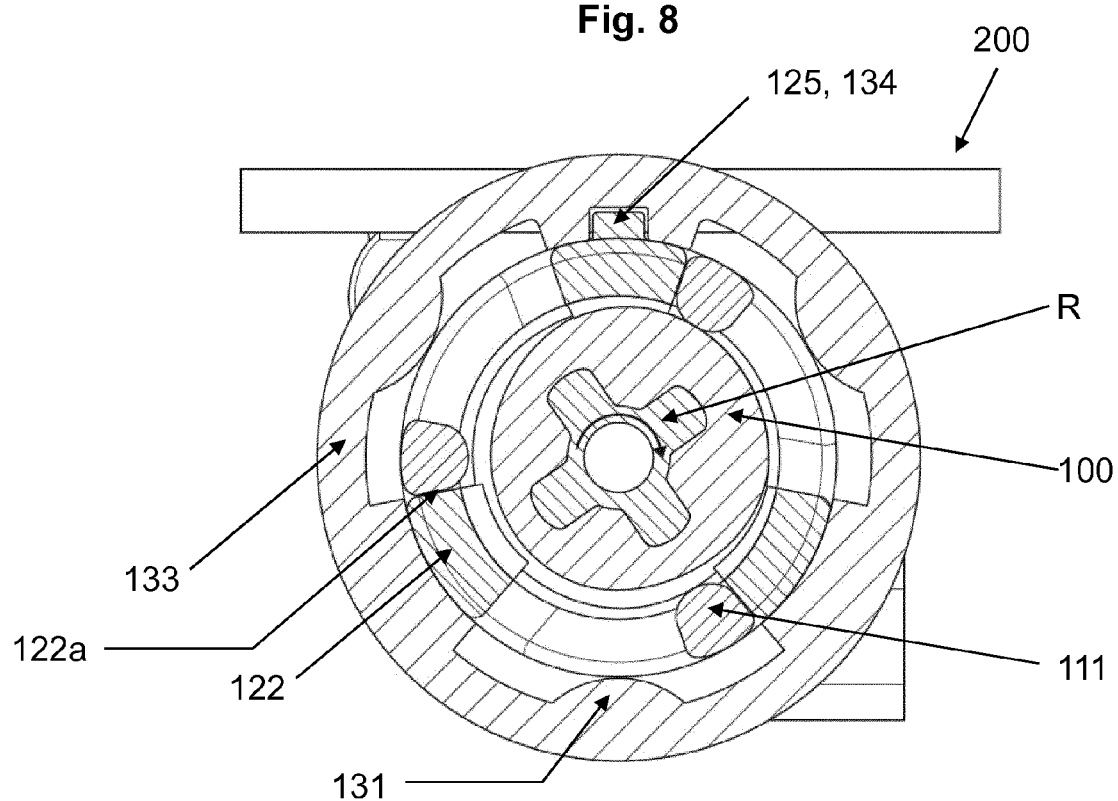
FIG. 9a-9e illustrate a valve switching sequence.

FIG. 9a shows the situation when the rotational direction of the drive, that is, the direction of the drive torque that is applied to the central member 100, is reversed. It is assumed that, prior to the situation as shown in FIG. 9a, the central member 100 has been rotated in a counter-clockwise direction (counter to the direction as indicated by arrow R) and now starts rotation in the clockwise direction (into the direction as indicated by arrow R). In the situation as shown in FIG. 9a, the valve member aperture is in alignment and fluidically coupled with the inlet aperture as explained before.

Assuming the outer thread 102 and the inner thread 123 to be right-hand threads, the central member 100 has, prior to the situation shown in FIG. 9a, accordingly been moved into the distal direction, thus increasing the liquid-filled volume of the dosing unit 1 as explained before. It can further be seen from FIG. 9a that the coupling pins 111 each abut a corresponding coupling pin block 122a. The situation of FIG. 9a further corresponds to the situation as shown in FIG. 1 with the rim 125 abutting the upper blocking edge 202a.

As a driving torque is applied in the direction R as shown in FIG. 9a, the central member begins a screw-like motion to the proximal direction. Due to the frictional engagement of the coupling pins 111 with the central member 100 as explained before, a corresponding movement is carried out by the coupling member 110, with the threaded central member section 102 and the coupling pins 111 being in sticking frictional engagement. The sleeve member 130 and the valve member 120, in contrast, do not move and maintain their position.

Figure 9B:
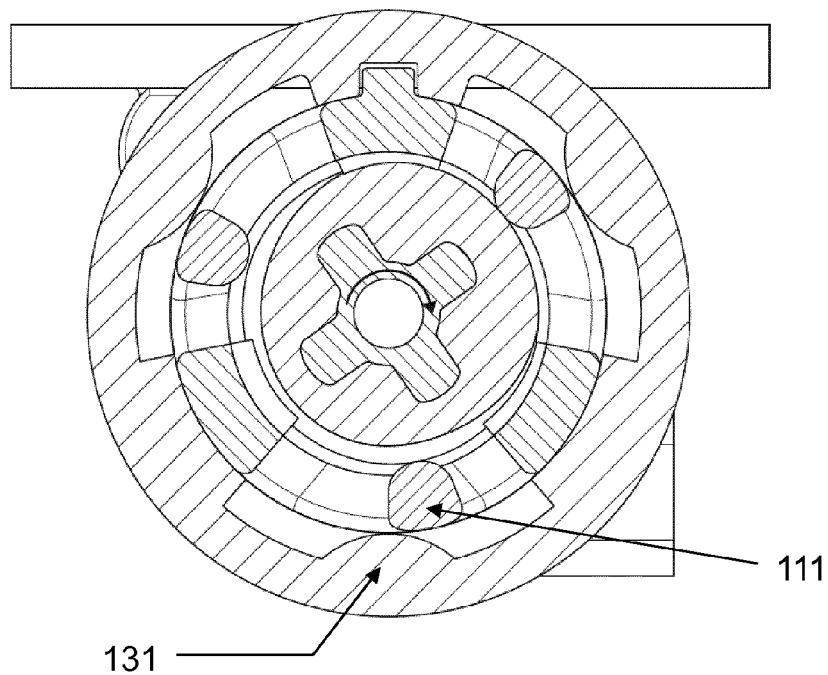

As the driving torque is further applied into the direction R, the coupling pins 111 will come in contact with the clamping members 131. This situation is shown in FIG. 9b.

Figure 9C:
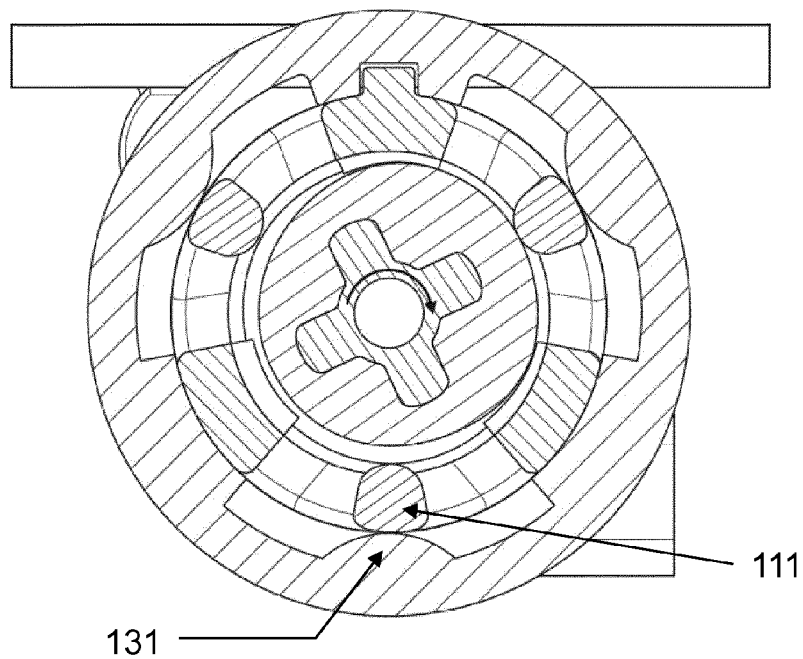

As the driving torque is still further applied into the direction R, the driving pins 111 are being aligned with clamping members 131 and are accordingly clamped between the clamping members 131 and the central member 100, resulting in the coupling pins 111 being in sticking frictional engagement with both the clamping members 131 (and, accordingly, the sleeve member 130 as a whole), and the central member 100. This situation is shown in FIG. 9c. The change from the situation of FIG. 9b to the situation of FIG. 9c corresponds to a change of the valve clutch device from the unengaged to the engaged configuration.

As the driving torque is still further applied into the direction R, the central member 100, the coupling member 110 and the sleeve member 120 will, due to the before-explained clamping, rotate together into the direction R. Since the valve member 120 is, via the engagement of the rim 125 with the notch 134 and via the engagement of the protrusions 124 with the sleeve slots 132, coupled to the sleeve member 130, the valve member carries out the same rotational movement and accordingly rotates within the stationary member recess 201. The contact between the rim 125 and the blocking edge 202*a* is cancelled as the valve member 120 starts moving.

Figure 9D:
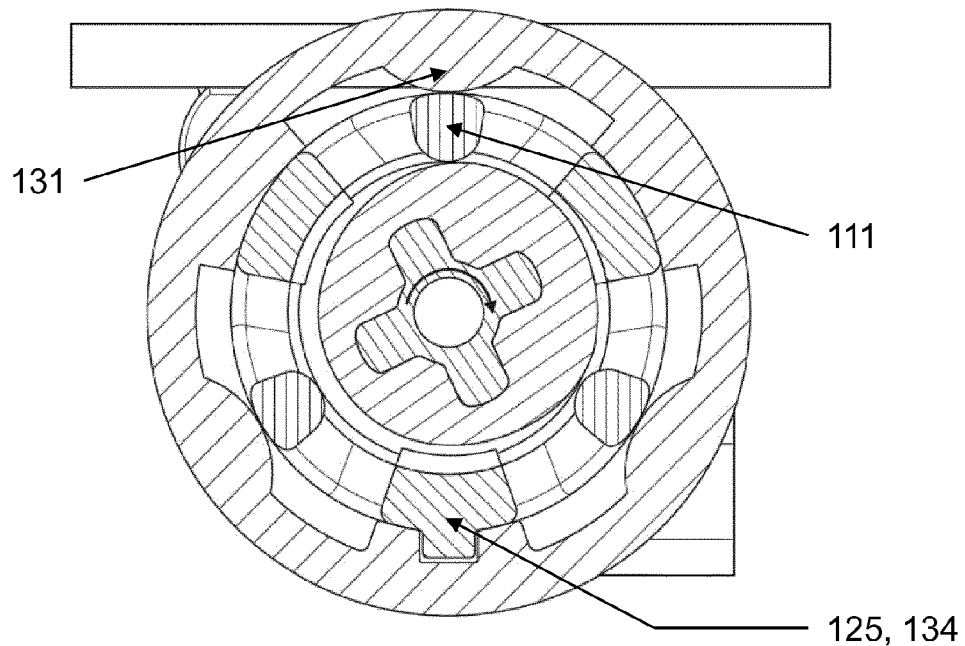

As the driving torque is still further applied into the direction R, the rim 125 will, after a rotation about 180°, abut the lower blocking edge 202*b*, thereby preventing further movement of the valve member 120 and the sleeve member 130. This situation is shown in FIG. 9*d*. In this situation, the valve member aperture is aligned with the outlet aperture.

As the driving torque is still further applied into the direction R, clamping of the clamping pins 111 will be cancelled, and the central member 100 and coupling member 110 further rotate in sticking frictional engagement, while sleeve member 120 and the valve member maintain their position. The cancelling of the clamping corresponds to a change of the valve clutch device from the engaged into the unengaged configuration.

Figure 9E:
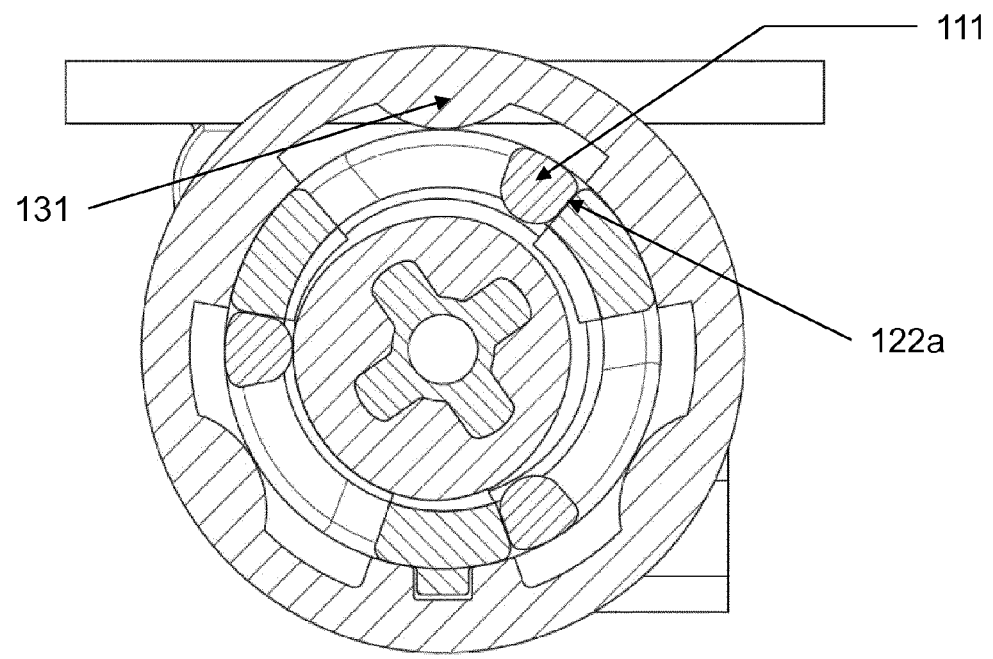

Finally, the coupling pins 111 hit and thereby abut again coupling pin blocks 122*a* as shown in FIG. 9*e*. With the coupling pins 111 abutting the coupling pin blocks 122*a*, the valve switching is finished. By comparing the situation as shown in FIG. 9*e* with the situation as shown in FIG. 9*a*, it can be seen that the configurations are largely identical, except that the sleeve member 130 (and the valve member 120) are rotated by 180° and the coupling pins 111 abut different coupling pin blocks 122*a*.

Subsequently further applying a driving torque into the direction R will result in only the central member carrying out a screw-like movement into the proximal direction, thus reducing the liquid-filled volume of the dosing unit 1 as explained before. During the further screw-like movement of the central member 100, the coupling pins 111 are, due to their blocking by the coupling pin blocks 122*a*, in sliding frictional engagement with the central member 100.

If the direction of the driving torque is reversed, the before-mentioned steps will be run through in the reverse order and the dosing unit will be switched from the outlet valve position into the inlet valve position.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A valve clutch device, comprising:
   a central member extending along a central axis and including a drive coupler, the drive coupler configured to receive a driving torque about the central axis;
   a coupling member including at least one coupling pin extending parallel to the central axis;
   a valve member rotatably disposed around the central axis between an inlet valve position and an outlet valve position;
   a sleeve member configured to rotationally engage the valve member, the sleeve member including at least one clamping member;
   an unengaged configuration wherein a driving torque received by the central member is not transmitted to the sleeve member; and
   an engaged configuration wherein the at least one coupling pin is clamped between the central member and the at least one clamping member, thereby transmitting the driving torque that is received by the central member via the sleeve member to the valve member, whereby the central member rotates with the valve member in the engaged configuration;
   wherein the valve clutch device is reversibly changeable between the engaged and unengaged configurations.

2. Valve clutch device according to claim 1, wherein the at least one coupling pin is frictionally engaged with the central member.

3. Valve clutch device according to claim 2, wherein the frictional engagement of the at least one coupling pin and the central member is changeable between a sliding frictional engagement and sticking frictional engagement as a function of an angular position of the at least one coupling pin relative to the central member and/or as a function of direction of rotation of the central member around the central axis.

4. Valve clutch device according to claim 1, further comprising angularly spaced coupling pin blocks and one of the clamping members arranged angularly symmetrically between two adjacent coupling pin blocks.

5. Valve clutch device according to claim 4, wherein the coupling pin blocks are formed by arm members of the valve member, the arm members extending generally parallel to the central axis.

6. Valve clutch device according to claim 1, wherein the coupling member includes a plurality of coupling pins and the clamping member includes a corresponding plurality of associated clamping members.

7. Valve clutch device according to claim 1, wherein the central member includes a threaded central member section with an outer thread and the valve member includes a corresponding inner thread.

8. Valve clutch device according to claim 1, further comprising a valve member block that blocks rotational movement of the valve member in the inlet valve position and the outlet valve position, respectively.

9. Valve clutch device according to claim 1, wherein the coupling member includes a coupling member base that is rotatably arranged around the central member with the at least one coupling pin projecting from the coupling member base.

10. Valve clutch device according to claim 1, wherein the central member, the coupling member, the clamping member and the valve member are coaxially arranged with the central axis.

11. Valve clutch device according to claim 1, wherein the central member is in sealing and sliding engagement inside the valve member, the central member thereby acting as a piston member.

12. Valve clutch device according to claim 1, wherein the drive coupler is configured to receive a drive pin in sliding engagement along the central axis and in substantially rigid rotational engagement with respect to the central axis.

13. Valve clutch device according to claim 1, wherein the valve member includes a cylinder and a valve member aperture in fluidic communication with an inner volume of the cylinder.

14. Liquid drug dosing unit, comprising:
   a valve clutch device according to claim 13; and a stationary member bearing the valve member sealingly and rotatably around the central axis, the stationary member including an inlet aperture and an outlet aperture, wherein the valve member aperture is in fluidic communication with the inlet aperture in the inlet valve position and alternatively in fluidic communication with the outlet aperture in the outlet valve position.

\* \* \* \* \*